(12) United States Patent
Dickmann

(10) Patent No.: US 7,581,657 B2
(45) Date of Patent: Sep. 1, 2009

(54) BANDAGE DISPENSER

(76) Inventor: Alexander J. Dickmann, 2220 Park Ave., Blue Springs, MO (US) 64015

( * ) Notice: Subject to any disclaimer, the term of this patent is extended or adjusted under 35 U.S.C. 154(b) by 536 days.

(21) Appl. No.: 11/434,531

(22) Filed: May 15, 2006

(65) Prior Publication Data

US 2007/0272575 A1    Nov. 29, 2007

(51) Int. Cl.
*G07F 11/00* (2006.01)
(52) U.S. Cl. ............... 221/88; 221/8; 221/87; 221/119; 221/120; 221/121
(58) Field of Classification Search .......... 221/119, 221/120, 121, 87, 88
See application file for complete search history.

(56) References Cited

U.S. PATENT DOCUMENTS

| | | | |
|---|---|---|---|
| 3,664,594 A | 5/1972 | Novak | |
| 4,662,637 A | 5/1987 | Pfeiffer | |
| 4,667,959 A | 5/1987 | Pfeiffer et al. | |
| 4,993,586 A | 2/1991 | Taulbee et al. | |
| 5,014,875 A * | 5/1991 | McLaughlin et al. | 221/2 |
| 5,065,894 A | 11/1991 | Garland | |
| 5,431,299 A | 7/1995 | Brewer et al. | |
| 5,435,459 A * | 7/1995 | Huck et al. | 221/70 |
| 5,499,740 A | 3/1996 | Huck et al. | |
| 6,213,343 B1 | 4/2001 | Damikolas | |
| 6,299,018 B1 | 10/2001 | Kimbrell | |
| 6,651,840 B1 * | 11/2003 | Van Dullemen et al. | 221/88 |
| 7,108,153 B2 * | 9/2006 | Wood | 221/15 |
| 2003/0019882 A1 | 1/2003 | Vogt et al. | |
| 2003/0047566 A1 | 3/2003 | DeVita | |
| 2004/0238559 A1 | 12/2004 | Ross | |
| 2005/0109789 A1 | 5/2005 | Nagayoshi | |
| 2005/0247722 A1 | 11/2005 | Blocker | |
| 2005/0258183 A1 | 11/2005 | Fienup et al. | |

* cited by examiner

*Primary Examiner*—Gene Crawford
*Assistant Examiner*—Timothy R Waggoner
(74) *Attorney, Agent, or Firm*—John C. McMahon

(57) ABSTRACT

A bandage dispenser comprising a housing having a magazine rotatably mounted therein; an advancement assembly for rotating the magazine and a pusher mechanism. The magazine including a plurality of sterile individual pie shaped compartments each receiving a sterile bandage assembly. The pusher mechanism sequentially penetrating the compartments and ejecting the bandage assembly therefrom after each compartment is aligned with the pusher mechanism by the advancement assembly. The advancement assembly including a ratchet mechanism on the magazine and an advancement solenoid.

10 Claims, 4 Drawing Sheets

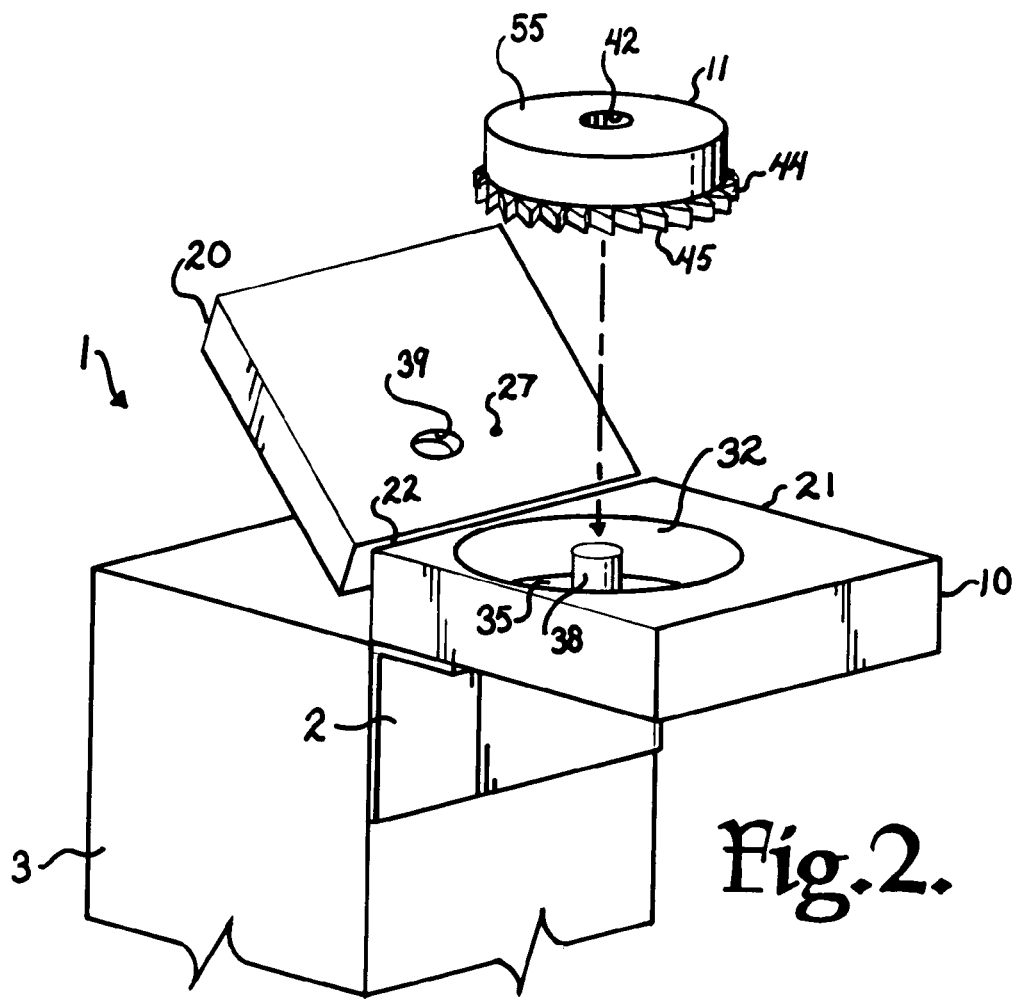
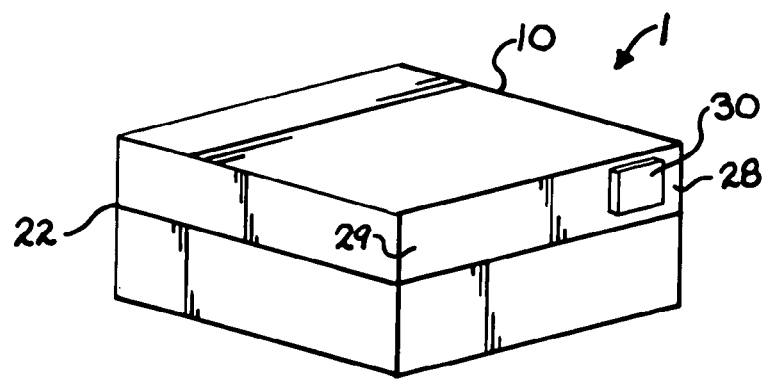

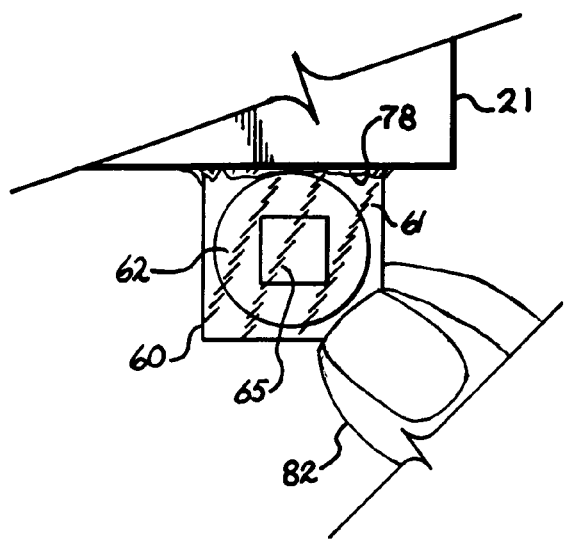
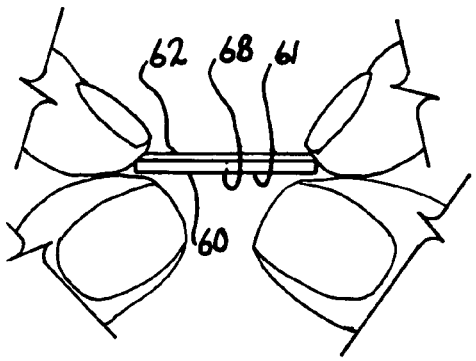
Fig. 7.  Fig. 8.
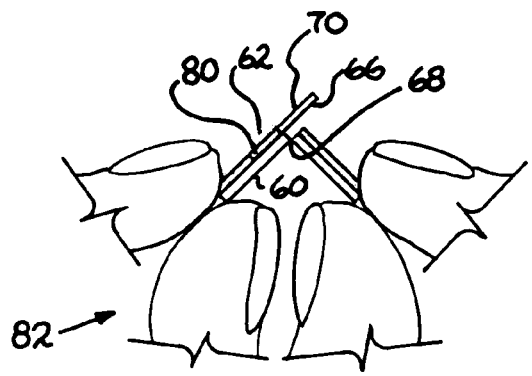
Fig. 9.

BANDAGE DISPENSER

BACKGROUND OF THE INVENTION

The present application is directed to an on demand dispenser for sterile bandages and, in particular, to such a dispenser that dispenses bandages from a rotating magazine.

Many medical facilities utilize a large number of bandages for covering minor punctures or wounds. For example, nurses stations that give shots, especially flu shots during the start of flu season, or the like must obtain, prepare and apply a bandage over each syringe puncture. Likewise, stations that take blood for various tests and the like must cover the resulting puncture with a bandage. Often such bandages must be applied in rapid succession. Furthermore, the doctor, nurse or technician performing the medical procedure may have their hands at least partly occupied with vials or syringes and it is inconvenient to unwrap a conventional bandage from its sterile packaging and then apply it to the patient.

Therefore, it is desirable to have a dispensing apparatus that quickly and easily provides a sterile bandage that is free of wrapping on a rigid or semi rigid backing from which the bandage can be easily and quickly removed and applied to a patient, even using a single hand.

SUMMARY OF THE INVENTION

A sterile bandage dispenser includes a housing and a sterile bandage magazine. The magazine holds a plurality of bandages between top and bottom sterile but penetratable walls in a daisy wheel configuration such that the bandages are each in a separate compartment that extends radially outward from a central axis. Located on the exterior of the magazine or, alternatively, on a separate carriage for the magazine is a ratchet mechanism.

Supported by the housing and aligned to sequentially engage teeth of the ratchet mechanism is a first solenoid that has a plunger that operably engages one of the teeth on demand and advances the magazine to place the next bandage compartment over a discharge opening or slot. Once the first solenoid has advanced the magazine, a second solenoid is triggered. The second solenoid is located above the next in line full compartment and extends a plunger associated therewith upon receiving an indication that the magazine has advanced. The plunger of the second solenoid penetrates the cover at the top of the chamber, engages a bandage assembly and pushes the bandage assembly with bandage on the bandage holder or backing through the barrier or cover at the bottom of the chamber, so as to partially project from, but be held by the surrounding cover.

The medical provider then takes the bandage and holder. The holder is a rigid or semi rigid disc or plate with a central break region or area of weakness which allows the medical provider to bend the holder so that the bandage becomes loose on one side and can be easily removed to be applied to a patient.

OBJECTS OF THE INVENTION

Therefore, the objects of the present invention are: to provide a sterile bandage dispenser that easily and rapidly presents a bandage to a health care provider for application to patient such that the bandage requires little preparation by the provider before applying to the patient; to provide such a dispenser that utilizes a magazine of bandages that can be easily exchanged for a fresh magazine when empty and which maintains individual bandages sterile until needed; to provide such a dispenser having a rotating daisy wheel or magazine that has individual pie shaped compartments for each bandage and penetratable upper and lower foil covers that seal the compartments; to provide such a dispenser that has an advancer that rotates and indexes each compartment over a dispensing opening and a pusher that both directly or indirectly penetrates the covers on each compartment and discharges the bandage from the compartment through a dispensing opening to allow grasping by a health care provider; to provide such a dispenser in combination with bandages individually positioned on a stiff backing wherein the backing has a line of weakness therein that allows a provider to bend the backing and expose part of the bandage to facilitate removal of the bandage therefrom; and to provide such a dispenser that is especially easy to use, that expedites health care, that is comparatively inexpensive to produce and that is especially well suited for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a bandage dispenser in accordance with the present invention.

FIG. 2 is a perspective and exploded view of the bandage dispenser opened to insert a magazine and shown mounted on a support.

FIG. 7 is an enlarged and fragmentary side elevational view of the dispenser showing a bandage being removed therefrom by a hand of a user.

FIG. 8 is a front elevational view of the bandage shown being held by fingers of a user.

FIG. 9 is a front elevational view of the bandage similar to FIG. 8 except subsequent to bending a backing holding the bandage to expose a portion of the bandage.

DETAILED DESCRIPTION OF THE INVENTION

Figure 3:
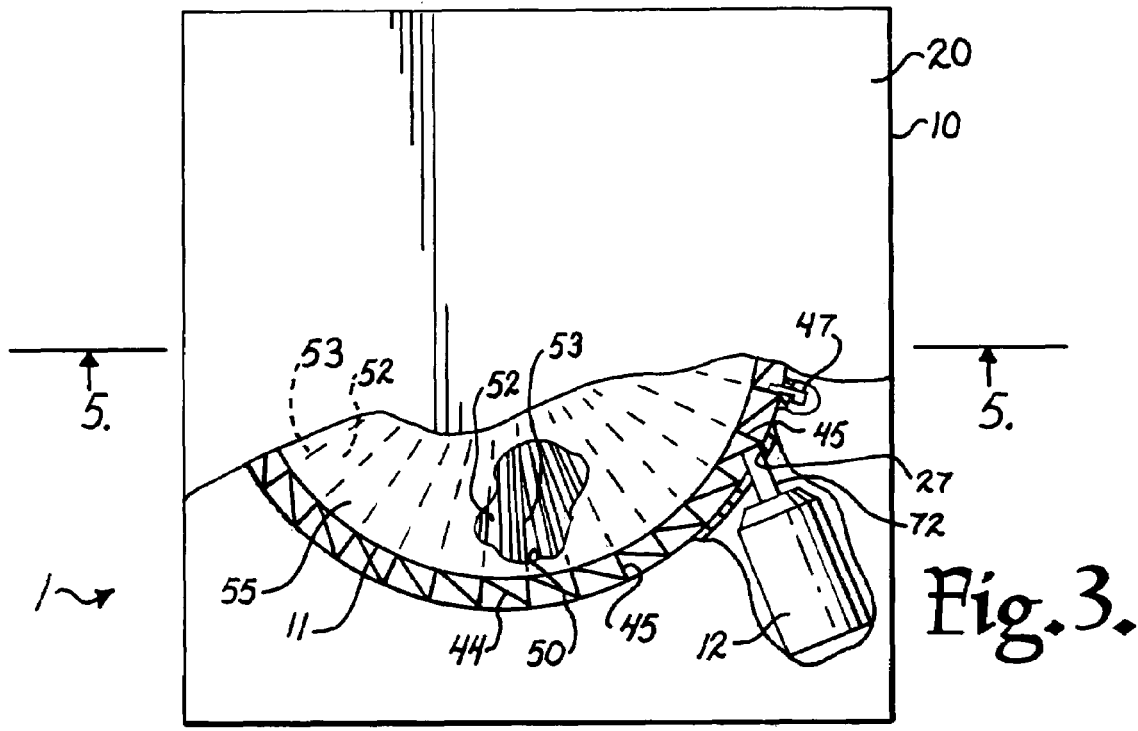
FIG. 3 is an enlarged top plan view of the dispenser with portions broken away to show the interior thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a bandage dispenser in accordance with the present invention mounted by a bracket 2 to a support 3. The particular structure of the support 3 is not of great importance as long as the dispenser 1 is accessible by a user and structures such as partial walls, cabinets or even independent dedicated stands can be used for the purpose.

The dispenser 1 includes a casing or housing 10, a magazine 11, an advancer 12, a pusher 13 and a control system 14.

The housing 10 is shown open in FIG. 2 attached to the support 3 and closed in FIG. 1. The housing 10 has rectangularly shaped upper and lower portions 20 and 21 joined along a rear thereof by a hinge 22, so that the upper portion 20 can be swung between a closed or covering position, as seen in FIG. 1, and an open or uncovering position, as seen in FIG. 1.

The control system 14 is mounted mainly in a hollow interior 25 of the upper portion 20. Also, the pusher 13 is mounted in the upper portion 20 and is located over an aperture 27 that allows the pusher 13 to function as will be described below. Located on a front end 28 of the upper portion is a wall 29 within which is mounted a push button type selector switch 30 that is part of the control system 14. The switch 30 is mounted so as to be accessible to a user from the front of the dispenser 1.

The control system 14 includes a power supply which is batteries in the present embodiment, but which can be a standard plug in type 120V AC supply also. The control system 14 is joined electrically to the advancer 12, pusher 13 and includes the selector switch 30.

The dispenser lower portion 21 is generally rectangular in outward shape forming an exterior boxlike structure and having an interior hollow cylindrical shaped magazine receiving opening 32 that has an axis A that is aligned so as to be generally vertical during use. The diameter of the opening 32 is somewhat smaller than the outer horizontal dimensions of the lower portion 21 and offset from center of the lower portion 21 to the left and rear slightly so as to create a space in the front right thereof to receive the pusher 13. The pusher 13 communicates with the opening 32 via an aperture 27.

Mounted on a bottom wall 35 of the lower portion 21 and extending upwardly therefrom is a magazine receiving spindle 38. The spindle 38 is cylindrically shaped and is coaxial with the axis A of the opening 32. The illustrated spindle 38 extends above an upper end of the lower portion 21 and into an opening 39 therefor in the upper portion 20 when in the closed position.

The lower portion bottom wall 35 also has a pass through dispensing slot 40 located therein and communicating with the lower portion opening 32. The slot 40 is located to cooperate with the magazine 11 and pusher 13, as will be discussed below.

The magazine 11 is a generally cylindrical shaped structure having a central circular bore 42 axially aligned and sized and shaped so as to rotatably receive the spindle 38. Located on the lower radially outer perimeter of the magazine 11 is a ratchet assembly 44 having a series of teeth 45 that are equally spaced and extend entirely around the magazine 11. The magazine 11 is designed to be easily changed out for another as described below and it is foreseen that the ratchet assembly 44 can be an integral part of the each magazine 11 or separately mounted to the remainder of the magazine 11 so that only an upper part of the magazine 11 is changed out or replaced. A frictional stop 47 operably engages the ratchet assembly 44 and prevents the magazine 11 from freewheeling, while allowing the magazine 11 to rotate incrementally the distance between adjacent teeth under control of the controller 14.

The magazine 11 has a generally hollow interior 50 separated into a plurality of pie shaped compartments or chambers 52 by radially extending dividers 53. An upper cover 55 and a lower cover 56 are sealably joined to the top and bottom of the magazine 11 respectfully and also sealably join with opposite sides of each divider 53 so that the chambers 52 can each be initially sterile and maintained as such until use. The covers 55 and 56 are constructed of paper, aluminum foil or the like that can be easily penetrated by use of force, but which retains the sterile aspects of the chambers 52 until a specific chamber 52 is penetrated.

Located in each of the chambers 52 is a bandage assembly 60. Each bandage assembly 60 includes a backing 61 and a bandage 62. In the illustrated embodiment, the bandages 62 are circular having a central pad 65 and an adhesive surface 66 surrounding the pad 65. The bandages 62 are of a conventional type and it is foreseen that other sizes and shapes can be used in accordance with the invention.

The backing 61 is constructed of a stiff (semi rigid) or rigid material such as plastic or the like that allows a respective bandage 62 to removably adhere to a surface 67 thereof. Centrally located on the backing 61 is a weakened line or region 68 that extends entirely across the backing 61. The region 68 allows a user to bend and break the backing 61 along the region 68 after removal from the dispenser 1 and as is seen in FIG. 9, so as to separate and expose half 70 of an associated bandage 62 from the backing 61 and thereby allow easy removal by the user for transfer to a patient.

The illustrated advancer 12 is a solenoid having a plunger 72 that extends outwardly when the advancer 12 is activated. The plunger 72 sequentially engages each tooth 45 of the ratchet assembly 44 and rotates the ratchet assembly 44 as required by the user.

Figure 4:
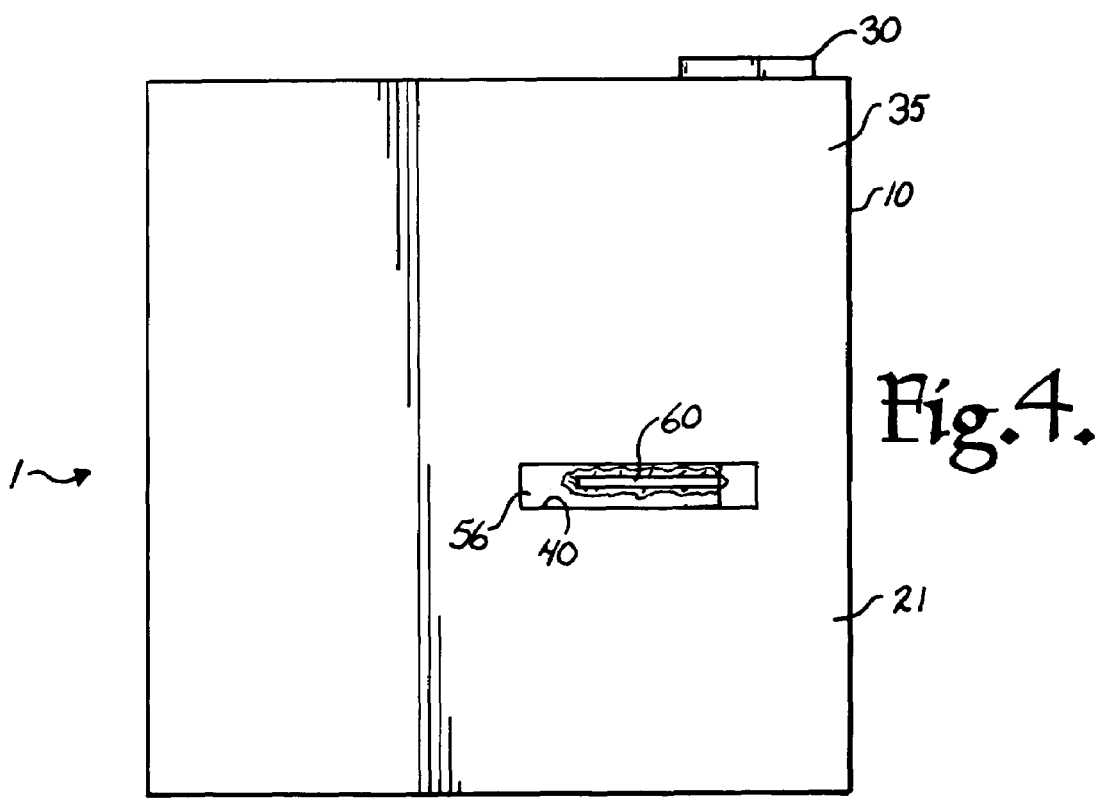
FIG. 4 is an enlarged bottom plan view of the dispenser.
Figure 6:
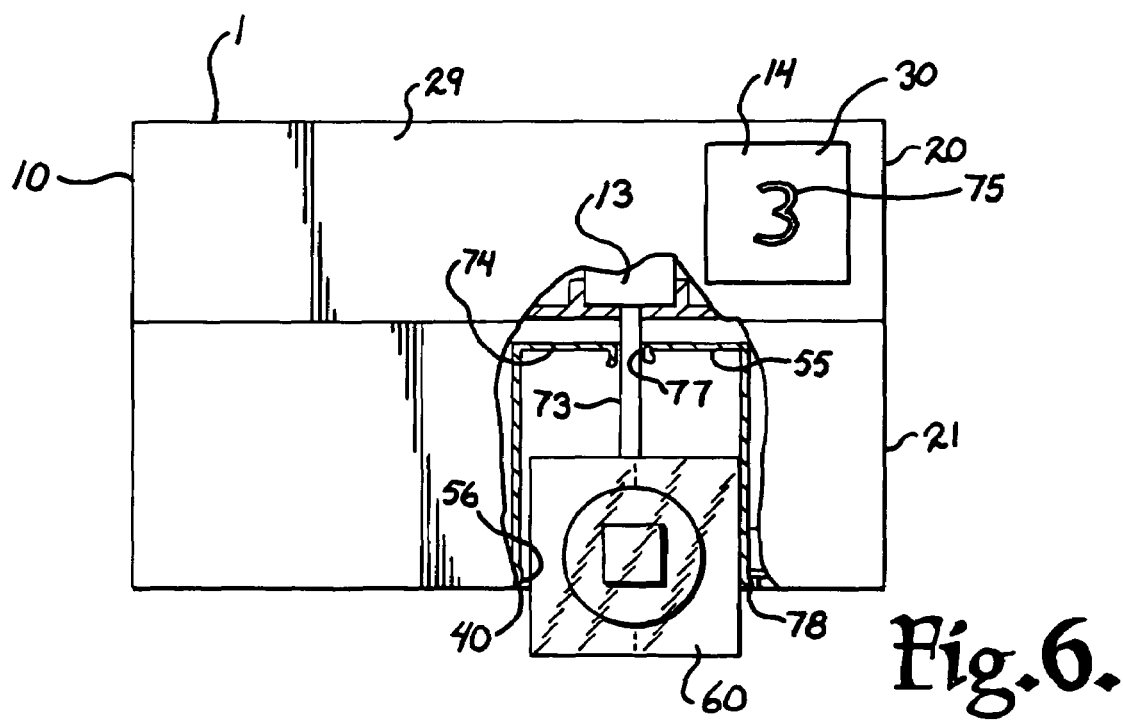
FIG. 6 is an enlarged front elevational view of the dispenser with portions broken away and showing discharge of a bandage thereof.

The illustrated pusher 13 is a solenoid having a plunger 73 that extends outwardly when the pusher 13 is activated. The plunger 73 is aligned so as to be located over a selected one 74 of said chambers 52 and the slot 40, such that when the pusher 13 is activated, the plunger 73 extends and first penetrates the upper cover 55, enters the selected one chamber 74 and engages the top of a bandage assembly 60. Thereafter, the pusher plunger 73 continues to extend thereby urging the bandage assembly 60 through the lower cover 56 and through the slot 40, such as is seen in FIGS. 4 and 6. It is foreseen that the advancer 12 and pusher 13 could be provided by other structure than solenoids that provide an equivalent function of rotating the magazine 11 and discharging the bandage assemblies 60 respectively.

The controller 14 includes an algorithm that subsequent to triggering the switch 30 by pushing inward thereon by a user, the controller 14 first triggers the advancer 12 to extend the plunger 72. A feedback system such as a light sensor checks to see if the magazine 11 rotated and, if it did, the pusher 13 is activated to dispense a bandage assembly 60. If the magazine 11 does not rotate, then the controller 14 first repeats and if the magazine 11 still does not rotate, the controller 14 signals for the operator to clear a jam before proceeding by flashing a display 75 on the switch 30.

Figure 5:
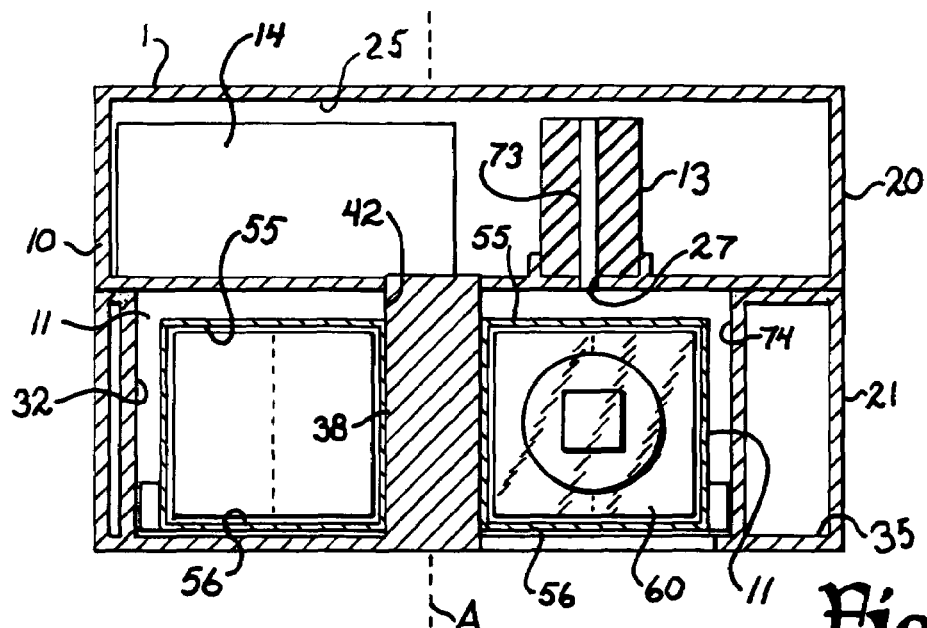
FIG. 5 is an enlarged cross sectional view of the dispenser, taken along line 5-5 of FIG. 3.

In use the dispenser 1 is initially configured by placing a new magazine 11 into the dispenser lower portion 21 and the upper portion 20 is closed over the lower portion 21, as seen in FIG. 1. The magazine 11 initially includes a bandage assembly 60 in each of the chambers 52 within which the assemblies 60 are positioned to be both generally vertically aligned and radially aligned relative to the spindle 38, as is seen in FIG. 5.

When a bandage 62 is needed by the user, the selector switch 30 is depressed. Preferably, the switch 30 has the display 75 which includes a LCD numeral counter thereon which tells the user how many bandages 62 are left in the current magazine. When the switch 30 is activated, the advancer 12 first extends the plunger 72 thereof which engages one of the teeth 45 on the ratchet assembly 44 and advances or rotates the magazine 11 one increment equal in radians to the size of each incremental chamber 52. Thereafter, the pusher 13 extends its plunger 73 which penetrates and passes through the upper cover 55 above a particular chamber 52, such as is seen in FIG. 6 at location 77. The pusher 13 continues to advance the plunger 73, also as seen in FIG. 6, so as to both engage an associated bandage assembly 60 and push the engaged bandage assembly 60 through the lower cover 56 at the location 78. The lower cover 56 rolls backward at location 78, but remains in sufficient frictional engagement with the assembly 60, so as to suspend it below the dispenser 1 and allow a user by the user's finger 82 to pull it downwardly to fully remove the assembly 60 from the dispenser 1, as seen in FIG. 7.

After removal from the dispenser 1, which is shown near completion in FIG. 7, the user grasps the assembly backing 61, as shown in FIG. 8 with the users fingers 82. Thereafter, the user bends the backing 61 so as to break the backing 61 along the weakened region 68, as seen in FIG. 9 to expose the bandage half 70. The user then grasps the bandage half 70 and removes a remainder 80 from the backing 61. Thereafter, the bandage 62 is applied to a patient. After all of the bandages 62 in a magazine 11 are utilized, the upper portion 22 is raised and the depleted magazine 11 is replaced with a new magazine 11.

It is to be understood that while certain forms of the present invention have been illustrated and described herein, it is not to be limited to the specific forms or arrangement of parts described and shown.

What is claimed and desired to be secured by Letters Patent is as follows:

1. A sterile bandage dispenser comprising:
a) a housing;
b) a magazine having a plurality of individual compartments with each compartment being sized and shaped to receive a bandage; each of said compartments being covered by a penetratable sterile seal; said magazine being removably mounted in said housing;
c) an advancement assembly that sequentially advances the compartments of the magazine so as to be aligned with a discharge opening; and
d) a pusher having a mechanically operated plunger that is selectively controllable by a user to sequentially penetrate the seal when each compartment is individually aligned with the discharge opening on demand of a user and discharge a bandage from the compartment aligned with the discharge opening.

2. A sterile bandage dispenser comprising:
a) a housing having upper and lower portions joined by a hinge; said lower portion including a discharge slot and having a spindle mounted therein;
b) a circular magazine having a plurality of pie shaped compartments with each compartment containing a bandage assemble; each of said compartments being sealably covered by upper and lower penetratable foils; said magazine including a ratchet assembly having a plurality of teeth equal in number to said compartments and extending around said magazine perimeter; said magazine having a central bore that is sized and shaped to be rotatably received on said spindle;
c) a control mechanism including a selector switch for use by an operator;
d) an advancement solenoid with an advancement plunger; said advancement solenoid being positioned such that extension of said advancement plunger engages a tooth of said ratchet assembly and rotates said magazine the equivalent width of one of said compartments; said advancement plunger being connected to said control mechanism;
e) a pusher solenoid having a pusher plunger and located so as to be positioned in alignment with said slot and so as to be over one of said compartments such that activation of said pusher solenoid extends said pusher plunger and penetrates said upper foil thereafter engaging an associated bandage assembly and urging same through the lower foil and from the respective compartment and through said slot; said pusher solenoid being controlled by said control mechanism and being synchronized with said advancement pusher such that said advancement pusher first algins a particular compartment with said pusher solenoid and thereafter said pusher solenoid pushes an associated bandage assembly from said particular compartment; and wherein
f) each bandage assembly includes a stiff backing with a bandage mounted thereon; each said backing having a centrally located region of weakness adapted to allow a user to bend said backing so as to expose a portion of a respective bandage for removal by the user.

3. A sterile bandage dispenser comprising:
a) a housing;
b) a magazine having a plurality of individual compartments with each compartment being sized and shaped to receive a bandage; each of said compartments being covered by a penetratable sterile seal; said magazine being removably mounted in said housing;
c) an advancement assembly that sequentially advances the compartments of the magazine so as to be aligned with a discharge opening; and
d) a pusher selectively controllable by a user to sequentially penetrate each compartment on demand of a user and discharge a bandage therefrom; said pusher comprising a pusher solenoid having a pusher plunger aligned such that upon extension of said pusher plunger, said pusher plunger penetrates a respective seal of one of the compartments positioned adjacent to the pusher plunger and discharges the bandage from the adjacent compartment.

4. The dispenser according to claim 3 wherein:
a) said magazine is circular and said compartments are pie shaped; said magazine being rotatably mounted in said housing.

5. The dispenser according to claim 4 wherein said advancement assembly includes:
a) a ratchet assembly with a tooth associated with each compartment cooperating with said magazine so as to rotate said magazine on demand; and
b) an advancement solenoid with an advancement plunger that sequentially engages the teeth so as to advance said magazine.

6. The dispenser according to claim 5 including:
a) a resistance stop to frictionally resist rotation of said magazine except by said advancement plunger.

7. The dispenser according to claim 3 wherein:
a) said magazine is circular with a central bore; and
b) said housing includes a spindle mounted therein that is rotatably received in said magazine bore.

8. The dispenser according to claim 3 in combination with a plurality of sterile bandage assemblies wherein each bandage assembly includes a stiff backing and one of said assemblies is located in each of said compartments.

9. The dispenser according to claim 8 wherein:
a) each bandage assembly backing has a medial region of weakness so as to be adapted to be bent thereat; and wherein
b) a respective bandage associated with each backing is partially exposed for grasping and removal when said backing is bent.

10. A sterile medical device dispenser comprising:
a) a housing;
b) a magazine having a plurality of individual compartments with each compartment being sized and shaped to receive a medical device; each of said compartments being covered by a penetratable sterile seal; said magazine being removably mounted in said housing;
c) an advancement assembly that sequentially advances the compartments of the magazine so as to be aligned with a discharge opening; and
d) a pusher selectively controllable by a user to sequentially penetrate each compartment on demand of a user and discharge a medical device therefrom; said pusher comprising a pusher solenoid having a pusher plunger aligned such that upon extension of said pusher plunger, said pusher plunger penetrates a respective seal of one of the compartments positioned adjacent to the pusher plunger and discharges the medical device from the adjacent compartment.

* * * * *

UNITED STATES PATENT AND TRADEMARK OFFICE
CERTIFICATE OF CORRECTION

PATENT NO. : 7,581,657 B2 Page 1 of 1
APPLICATION NO. : 11/434531
DATED : September 1, 2009
INVENTOR(S) : Alexander J. Dickmann It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 575 days.

Signed and Sealed this

Fourteenth Day of September, 2010

David J. Kappos
*Director of the United States Patent and Trademark Office*